US010568681B2

(12) United States Patent
Hermann Fakler

(10) Patent No.: US 10,568,681 B2
(45) Date of Patent: Feb. 25, 2020

(54) GUIDE ASSEMBLY FOR FORCEPS

(71) Applicant: Sutter Medizintechnik GmbH, Freiburg (DE)

(72) Inventor: Michael Otto Hermann Fakler, Freiburg (DE)

(73) Assignee: Sutter Medizintechnik GmbH, Freiburg (DE)

( * ) Notice: Subject to any disclaimer, the term of this patent is extended or adjusted under 35 U.S.C. 154(b) by 243 days.

(21) Appl. No.: 15/460,504

(22) Filed: Mar. 16, 2017

(65) Prior Publication Data
US 2017/0265932 A1    Sep. 21, 2017

(30) Foreign Application Priority Data

Mar. 16, 2016 (DE) .................. 10 2016 104 888

(51) Int. Cl.
*A61B 18/04* (2006.01)
*A61B 18/14* (2006.01)
*A61B 90/11* (2016.01)
*A61B 90/00* (2016.01)
(Continued)

(52) U.S. Cl.
CPC .......... *A61B 18/1442* (2013.01); *A61B 17/28* (2013.01); *A61B 90/08* (2016.02); *A61B 90/11* (2016.02); *A61B 2017/2825* (2013.01); *A61B 2018/00083* (2013.01); *A61B 2090/034* (2016.02)

(58) Field of Classification Search
CPC .. A61B 2018/00172; A61B 2018/1462; A61B 2017/29; A61B 17/29; A61B 17/30; A61B 2017/2825; A61B 2090/034; A61B 90/11; F16B 21/06; B65D 59/02; B65D 53/02
See application file for complete search history.

(56) References Cited

U.S. PATENT DOCUMENTS 3,578,200 A  *  5/1971  Hetzer ............... B65D 39/0023
                                                       138/96 T
6,286,699 B1 *  9/2001  Sudo ...................... B65D 39/00
                                                       215/247
(Continued)

OTHER PUBLICATIONS http://wheaton.com/media/catalog/category/rubber-stoppers.jpg Current operator of website DWK Life Sciences Captured by Wayback Machine (https://web.archive.org/web/20130511023556/http://wheaton.com/media/catalog/category/rubber-stoppers.jpg) on May 11, 2013 (Year: 2013).*

*Primary Examiner* — Daniel W Fowler
(74) *Attorney, Agent, or Firm* — Budzyn IP Law, LLC

(57) ABSTRACT

The invention relates to a guide assembly for an instrument comprising two legs, in particular forceps, the guide assembly comprising first and second guide elements, wherein the guide elements each comprise a base body, provision being made in each case on the outer side of the base body for an arrangement for snapping into place in an opening on an inner side of the legs of the instrument, provision being made on the inner side of the base body in the case of the first guide element for a protrusion and in the case of the second guide element for a recess, which is complementary to the protrusion, and provision being made in each case for a hollow on the outer side of the base body of the first as well as the second guide elements.

12 Claims, 2 Drawing Sheets

(51) Int. Cl.
*A61B 17/28* (2006.01)
*A61B 18/00* (2006.01)

(56) References Cited

U.S. PATENT DOCUMENTS

| | | | |
|---|---|---|---|
| 6,406,485 B1 * | 6/2002 | Hossain | A61B 17/29 |
| | | | 606/151 |
| 7,513,897 B2 * | 4/2009 | Sutter | A61B 17/30 |
| | | | 606/210 |
| 8,828,047 B2 * | 9/2014 | Bissinger | A61B 17/30 |
| | | | 606/206 |
| 2006/0278653 A1 * | 12/2006 | Zeyfang | F16L 57/005 |
| | | | 220/801 |

* cited by examiner

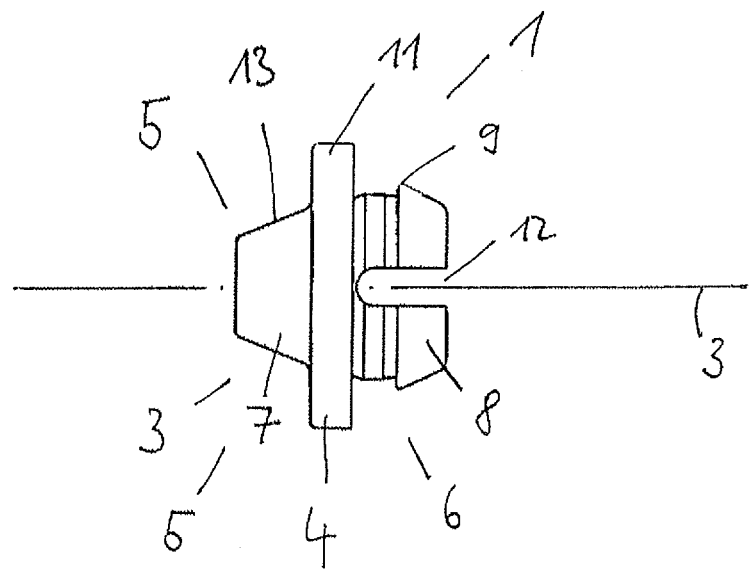
Figur 1
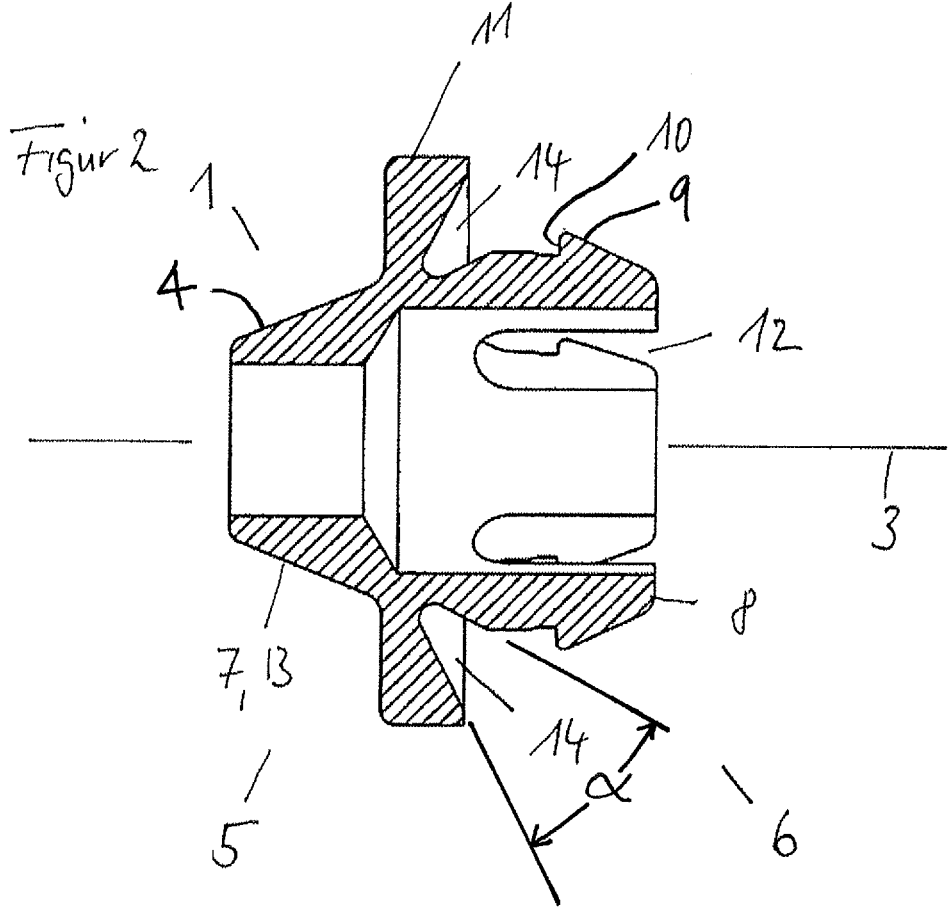
Figur 2

Figur 3
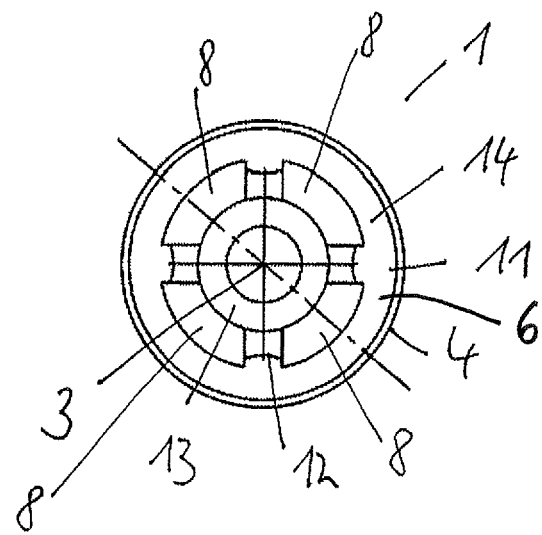
Figur 4
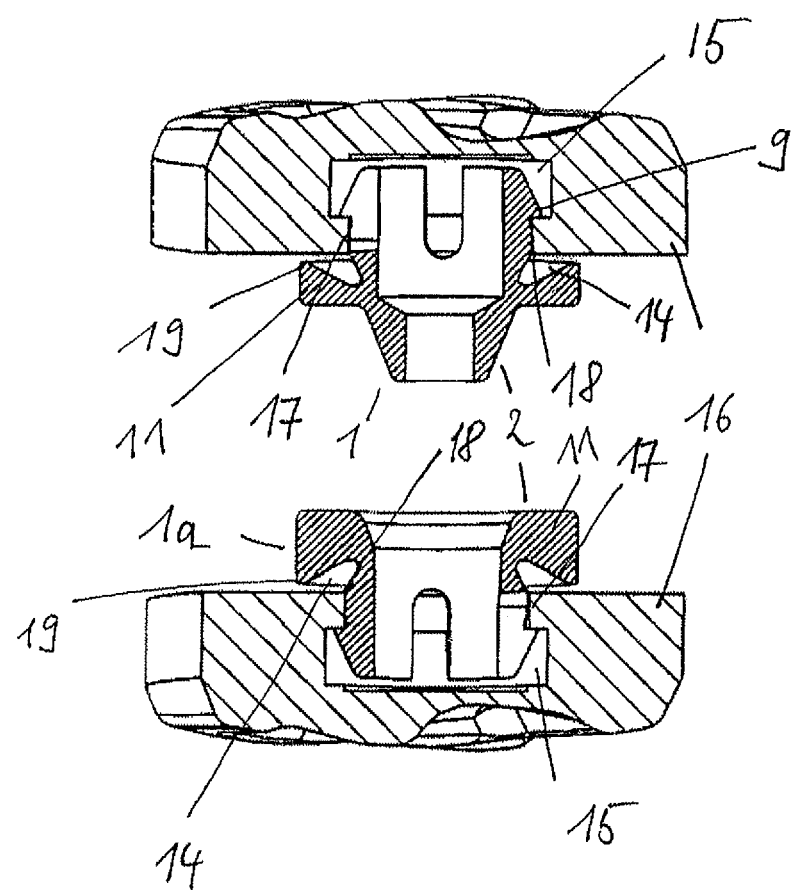

GUIDE ASSEMBLY FOR FORCEPS

FIELD OF THE INVENTION

The invention relates to a guide assembly for an instrument comprising two legs, in particular forceps, wherein the guide assembly includes first and second guide elements.

BACKGROUND

Guides for forceps are known. They serve the purpose of absorbing shearing forces, which may occur, when compressing the forceps, and of preventing a divergence of the forceps legs. For the most part, the guides are embodied as appendages and/or recesses of the legs of the forceps and consist of the same material as the forceps legs. If they are electrosurgical forceps, however, the guides must consist of insulating material in order to prevent a short-circuit when compressing the legs. The guides then can not be embodied in one piece with the forceps legs any longer. The surfaces of electrosurgical instruments are provided with an insulating coating for the same reason. In the production process, the thickness of the coating is subject to fluctuations.

Fluctuations of the layer thickness can make it more difficult to fasten the guides to the inner sides of the legs.

It is the object of the invention to create a guide assembly of the above-mentioned type, which provides for a good fastening to the inner sides of the legs of the forceps.

SUMMARY OF THE INVENTION

This object is solved by means of the invention specified in the independent claims. Advantageous further developments can be gathered from the subclaims.

To solve this object, what is created according to the invention is a guide assembly of the above-defined type, wherein the first and second guide elements in each case comprise a base body comprising an outer side and an inner side, provision is made in each case on the outer side of the base body in the case of the first as well as the second guide element for means for fastening, in particular snapping into place in an opening on an inner side of the legs of the instrument, provision is made on the inner side of the base body in the case of the first guide element for a protrusion and in the case of the second guide element for a recess, which is complementary to the protrusion, in the case of the first as well as the second guide element, the base body is in each case embodied to rest with its outer side against an inner side of the legs of the instrument, after being fastened to the instrument, and to form a collar around the opening in the inner side of the legs, and provision is in each case made in the area of the collar for a hollow on the outer side of the base body in the case of the first as well as the second guide elements.

The invention takes into account that material accumulates in response to the coating of the inner sides of the legs, in particular in the area of the openings. This material accumulation is caused by plugs, among others, which are inserted into the openings during the coating. As a result, prior art means for fastening cannot snap into place correctly, for example, because the prior art means for fastening cannot engage undercuts in the openings above a certain layer thickness about the openings.

The guide elements can be connected to the legs of the instrument in that they are snapped into place with openings, in particular blind holes comprising undercuts, which are provided on the inner sides of the legs. So as not to impact the accuracy of fit of the guide members in the blind holes, the inner walls of the blind holes are not coated in the production process. For this purpose, the blind holes are closed by means of a plug or the like during the coating. Each plug, however, can result in further inaccuracies with respect to the thickness of the coating on the inner sides of the legs in response to the coating. However, the hollow arranged on the base body of each of the guide elements has the result that the edge of the opening remains free, even after the guide element is inserted and snapped into place in the opening on the inner side of a forceps leg. Layer material accumulated about the edge of the opening is thus in the clearance formed by the hollow and does not lead to an impact of the tight fit of the guide element in the opening of the forceps leg. The fastening means can thus always engage with the opening with an accurate fit, regardless of possible fluctuations of the layer thickness about the edge of the opening.

Notwithstanding the above, layer thicknesses, which differ from part to part, can be created in response to the coating of the forceps legs. The hollow does not only create space for accumulations of the coating around the opening. Due to the fact that the hollow lends the collar certain elasticity, the guide elements can also still snap into place in the openings when the layer thickness varies. The elasticity resulting from the intentionally provided "weak point" in the area of the smallest material thickness on the collar thus also makes it possible to use the guide elements in the case of production tolerances of the coating of the forceps legs.

The hollow thus ensures the secure and accurate fit of the guide elements in the forceps legs.

In an embodiment of the invention, the base body of both guide elements is in each case embodied symmetrically to an axis of symmetry. The hollow forms a rotationally symmetrical depression in the collar on the outer side of the base body. The hollow can be designed according to DIN 509.

In an embodiment of the invention, the fastening means extend substantially parallel to an axis of symmetry of the base body on the outer side of the base body and have a nose-like holding protrusion comprising at least one shoulder, which is located opposite the collar and which is positioned vertical to the axis of symmetry. The fastening means thus make it possible to snap the base body into place in the opening and thus provide for a simple assembly.

Advantageously, the fastening means are spaced apart from one another, and the fastening means are in particular formed by a plurality of snap-in pins, which are separated from one another by means of slits. The gaps provide for the elastic yielding of the fastening means. The guide elements can thus be easily inserted into the openings.

In an embodiment of the invention, the protrusion and the recess, which is complementary thereto, is formed by means of an appendage on the first guide element or an opening, respectively, in the second guide element, in particular wherein the appendage has tapered, preferably conical shoulders, and the opening has at least partially tapered, preferably conically tapered inner walls for accommodating the appendage.

The conical shoulders of the protrusion and of the recess, which is complementary thereto, are designed in such a way that they can enter into a positive connection, so that during use of the forceps, divergence of the legs is prevented thereby maintaining the legs oriented relative to one another.

In an embodiment of the invention, the base body is embodied in one piece and forms a counter stop to the vertical shoulder of the nose-like holding protrusions. This embodiment can be produced in a particularly stable and simple manner.

In an embodiment of the invention, the hollow has an opening angle, the opening angle is in particular between 20° and 45° and preferably 35°. This embodiment turned out to be advantageous for the underlying application, in particular for the specific characteristics of the coating materials of forceps legs.

According to the invention, what is also created is an instrument comprising two legs, in particular electrosurgical forceps, comprising a guide assembly as described above, wherein the inner sides of the legs of the instrument in each case have openings located opposite one another, in which the first or the second guide element, respectively, of the guide assembly can in each case be fastened.

BRIEF DESCRIPTION OF THE DRAWINGS

Exemplary embodiments of the invention will be described in more detail below by means of the enclosed drawings.

FIG. 1 shows a side view of an exemplary embodiment of the invention;

FIG. 2 shows a sectional illustration along an axis of symmetry of an exemplary embodiment of the invention;

FIG. 3 shows a top view onto a side, which faces the forceps leg, of an exemplary embodiment of the invention;

FIG. 4 shows an application example of an exemplary guide element in forceps.

DESCRIPTION OF THE INVENTION

FIG. 1 shows a first guide element 1 of a guide assembly 2 including the first guide element 1 and a second guide element 1a in side view (see FIG. 4). The first guide element 1 consists of a base body 4, which is rotationally symmetrical to an axis of symmetry 3. The base body comprises an inner side 5 and an outer side 6.

A guide means 7, which is embodied as conically tapered appendage 13, is arranged on the inner side 5. The outer side 6 comprises means for fastening the guide assembly 2 to a blind hole 15 on the inner side of a forceps leg 16 (see FIG. 4). The fastening means are formed by snap-in pins 8, which extend on the outer side 6 of the base body 4, parallel to the axis of symmetry 3. The snap-in pins 8 have nose-like holding protrusion 9, which, based on the axis of symmetry 3, extend outwards at right angles. The holding protrusions 9 have a shoulder 10, which is positioned at right angles to the axis of symmetry 3 and which forms a counter stop to a collar 11, which circulates rotationally symmetrically on the base body 4. In the illustrated embodiment, the holding protrusions have shoulders, which are positioned at right angles to the axis of symmetry. In alternative embodiments, the shoulders can also have other angles with respect to the axis of symmetry. The snap-in pins 8 are arranged so as to be evenly distributed across a circumferential line of the base body 4 and are separated and spaced apart from one another by means of slits 12.

FIG. 2 shows a sectional illustration of the first guide element 1 along the axis of symmetry 3. The entire guide element 1 is formed from one material in one piece. The conically tapered appendage 13 on the inner side 5 of the base body 4 is embodied as a hollow truncated cone.

On its outer side, the base body 4 has a hollow 14. The hollow 14 is embodied radially circumferentially and rotationally symmetrical with respect to the axis of symmetry. The hollow 14 may have an opening angle α between 20° and 45° preferably 35°.

FIG. 3 shows a top view onto the outer side 6, which faces a forceps leg, of the base body 4 of the first guide element 1. Four snap-in pins 8 extend out of the image plane, parallel to the axis of symmetry 3. The snap-in pins 8 are arranged in a circular manner around the axis of symmetry 3 and are evenly distributed across the circumference. They are separated from one another by means of the slits 12.

The second guide element 1a is formed similarly to the first guide element 1, except that the guide means 7 on the second guide element 1a includes an opening complementarily formed to receive the appendage 13 of the first guide element 1 with the forceps legs 16 being in a closed state.

FIG. 4 shows the guide assembly 2 including the first guide element 1 and the second guide element 1a. The guide elements 1, 1a are inserted into the blind holes 15 on the leg inner side of the forceps legs 16 by means of the fastening means. The snap-in pins 8 engage behind the undercuts 17 by means of the holding protrusions 9. The first and the second guide elements 1, 1a are thus in each case snapped into place in the blind holes 15. The outer sides of the snap-in pins 8 thereby rest against an inner wall of the blind holes 15, which forms the undercut 17. The vertical shoulders 10 of the holding protrusions 9, which are preferably positioned at right angles to the axis of symmetry, together with the circumferential collar 11, thus form a positive connection of the guide elements 1, 1a with the forceps legs 16. The collar 11 and the holding protrusions 9 thereby form alternating counter stops.

The hollow 14 forms a depression in the base body 4, which revolves around an edge 18 of the blind hole 15. Due to the hollow 14, the edge of the blind hole 18 remains free, even when the guide element 1, 1a, is snapped into place, and is not touched by the circumferential collar 11. Space for possible material thickenings or—accumulations, which can be created in the area of the blind holes in response to the coating of the inner side of the forceps legs, is created by means of the hollow 14.

LIST OF REFERENCE NUMERALS 1 first guide element
1a second guide element
2 guide assembly
3 axis of symmetry
4 base body
5 inner side of the base body
6 outer side of the base body
7 guide means
8 snap-in pins
9 nose-like holding protrusions
10 vertical shoulder(s)
11 circumferential collar
12 slits/gaps
13 conical appendage
14 hollow
15 blind hole
16 forceps leg
17 undercuts
18 edge of the blind hole
19 outer area of the collar

The invention claimed is:

1. A forceps comprising two legs (16) and a guide member (2), the guide member (2) comprising a first and a second guide element (1, 1a), wherein:

the first and second guide elements (1, 1a) in each case comprise a base body (4) comprising an outer side (6) and an inner side (5), provision is made in each case on the outer side (6) of the base body (4) in the case of the first as well as the second guide element (1, 1a) for means for fastening (8), in particular snapping into place in an opening (15) on an inner side of the legs of the forceps (16), provision is made on the inner side (5) of the base body (4) in the case of the first guide element (1) for a protrusion (13) and in the case of the second guide element (1a) for a recess, which is complementary to the protrusion (13) to receive the protrusion (13) with insertion into the recess, in the case of the first as well as the second guide element (1, 1a), the base body (4) is in each case embodied to rest with its outer side (6) against an inner side of the legs (16) of the forceps, after being fastened to the forceps, and to form a collar (11) around the opening (15) in the inner side of the legs, and provision is in each case made in the area of the collar (11) for a hollow (14) on the outer side (6) of the base body (4) in the case of the first as well as the second guide elements (1, 1a).

2. The forceps according to claim 1, wherein, in each case, the hollow (14) forms a rotationally symmetrical depression in the collar (11) on the outer side of the base body (6).

3. The forceps according to claim 1, wherein the base body (4) of the first and second guide elements (1, 1a) is in each case symmetrical to an axis of symmetry (3).

4. The forceps according to claim 1, wherein the fastening means (8), in each case, extend substantially parallel to an axis of symmetry (3) of the base body on the outer side of the base body (6) and have nose-shaped holding protrusions (9) comprising at least one shoulder (10), which is located opposite the collar (11).

5. The forceps according to claim 4, wherein, the collar (11) is positioned at right angles to the axis of symmetry (3).

6. The forceps according to claim 4, wherein the fastening means (8) are formed by a plurality of snap-in pins (8), which are separated from one another by means of slits (12).

7. The forceps according to claim 6, wherein, the nose-shaped holding protrusions (9) are provided on the snap-in pins (8).

8. The forceps according to claim 4, wherein the base body (4) is embodied in one piece and the collar (11) acts as a counter stop to the shoulder (10) of the nose-shaped holding protrusions (9).

9. The forceps according to claim 8, wherein, in each case, the opening (15) on the inner side of the legs includes a radially-inwardly projecting undercut (17) with the collar (11) resting against a first face of the undercut (17) and the shoulder (10) resting against a second face, opposite to the first face, of the undercut (17), the first face of the undercut (17) being exposed to the hollow (14).

10. The forceps according to claim 1, wherein the protrusion (13) is formed by an appendage having tapered shoulders (13), and the recess is formed by an opening having at least partially tapered inner walls for accommodating the appendage (13).

11. The forceps according to claim 1, wherein, in each case, the hollow (14) has an opening angle between 20° and 45°.

12. The forceps according to claim 11, wherein, in each case, the hollow (14) has an opening angle of 35°.

* * * * *